(12) United States Patent
Tai et al.

(10) Patent No.: US 12,415,018 B2
(45) Date of Patent: Sep. 16, 2025

(54) MICROCAPILLARY MESH OXYGEN TRANSPORTER FOR CELL TRANSPLANTATIONS

(71) Applicants: California Institute of Technology, Pasadena, CA (US); City of Hope, Duarte, CA (US)

(72) Inventors: Yu-Chong Tai, Pasadena, CA (US); Kuang-Ming Shang, Pasadena, CA (US); Hirotake Komatsu, Temple City, CA (US)

(73) Assignees: California Institute of Technology, Pasadena, CA (US); Cite of Hope, Duarte, CA (US)

( * ) Notice: Subject to any disclaimer, the term of this patent is extended or adjusted under 35 U.S.C. 154(b) by 438 days.

(21) Appl. No.: 18/070,334

(22) Filed: Nov. 28, 2022

(65) Prior Publication Data
US 2023/0166004 A1 Jun. 1, 2023

Related U.S. Application Data

(60) Provisional application No. 63/283,639, filed on Nov. 29, 2021.

(51) Int. Cl.
*A61L 27/38* (2006.01)
*A61L 27/54* (2006.01)
*A61L 27/56* (2006.01)
*C12N 5/00* (2006.01)

(52) U.S. Cl.
CPC ........... *A61L 27/3804* (2013.01); *A61L 27/54* (2013.01); *A61L 27/56* (2013.01); *C12N 5/0068* (2013.01); *C12N 2533/30* (2013.01); *C12N 2535/10* (2013.01)

(58) Field of Classification Search
None
See application file for complete search history.

(56) References Cited

U.S. PATENT DOCUMENTS

| | | | |
|---|---|---|---|
| 11,284,987 | B2 | 3/2022 | Sostek |
| 11,458,012 | B2 | 10/2022 | Zopf et al. |
| 2016/0114079 | A1 | 4/2016 | Samaniego et al. |
| 2017/0086963 | A1* | 3/2017 | Tai .......................... A61F 2/022 |
| 2019/0254959 | A1 | 8/2019 | Tuch et al. |
| 2021/0283308 | A1* | 9/2021 | Komatsu ................ A61K 35/39 |
| 2022/0143271 | A1 | 5/2022 | Boughton et al. |

OTHER PUBLICATIONS

Lin, C.-W., et al., ACS Appl. Bio Mater. 3: 5678 à 5686 (2020). (Year: 2020).*
"Microcapillary Parylene-HT Mesh", References for Mark, Nov. 3, 2022, 8 pages.
Atkinson et al., "Type 1 Diabetes", Lancet, vol. 383, No. 9911, Jan. 4, 2014, pp. 69-82.
Bian et al., "MD Simulation and Cluster Analyses of the Gas Permeability of Parylene AF4 Membranes", Journal of Molecular Structure, vol. 1105, Feb. 5, 2016, pp. 142-151.
Brunelle et al., "Meta-Analysis of the Effect of Insulin Lispro on Severe Hypoglycemia in Patients With Type 1 Diabetes", Diabetes Care, vol. 21, No. 10, Oct. 1998, pp. 1726-1731.
Colton , "Oxygen Supply to Encapsulated Therapeutic Cells", Advanced Drug Delivery Reviews, vols. 67-68, Apr. 2014, pp. 93-110.
Komatsu et al., "A Subcutaneous Pancreatic Islet Transplantation Platform Using a Clinically Applicable, Biodegradable Vicryl Mesh Scaffold—an Experimental Study", Transplant International, vol. 33, No. 7, Jul. 2020, pp. 806-818.
Komatsu et al., "Oxygen Environment and Islet Size Are the Primary Limiting Factors of Isolated Pancreatic Islet Survival", PLoS One, vol. 12, No. 8, Aug. 23, 2017, pp. 1-17.
Komatsu et al., "Posttransplant Oxygen Inhalation Improves the Outcome of Subcutaneous Islet Transplantation: a Promising Clinical Alternative to the Conventional Intrahepatic Site", American Journal of Transplantation, vol. 18, No. 4, Apr. 2018, pp. 832-842.
Ludwig et al., "Favorable Outcome of Experimental Islet Xenotransplantation without Immunosuppression in a Nonhuman Primate Model of Diabetes", PNAS, vol. 114, No. 44, Oct. 31, 2017, pp. 11745-11750.
Pedrazaa et al., "Preventing Hypoxia-induced Cell Death in Beta Cells and Islets via Hydrolytically Activated, Oxygen-generating Biomaterials", PNAS, vol. 109, No. 11, Mar. 13, 2012, pp. 4245-4250.
Ricordi , "Islet Transplantation: A Brave New World", Lilly Lecture 2002, Diabetes, vol. 52, No. 1, Jul. 2003, pp. 1595-1603.
Ryan et al., "Continued Insulin Reserve Provides Long-Term Glycemic Control", Successful Islet Transplantation, Diabetes, vol. 51, No. 7, Jul. 2002, pp. 2148-2157.
Shapiro et al., "Islet Transplantation in Seven Patients with Type 1 Diabetes Mellitus Using a Glucocorticoid-Free Immunosuppressive Regimen", The New England Journal of Medicine, vol. 343, No. 4, Jul. 7, 2000, pp. 230-238.

* cited by examiner

*Primary Examiner* — David J Blanchard
*Assistant Examiner* — Daniel F Coughlin
(74) *Attorney, Agent, or Firm* — Mark P. Mathison

(57) ABSTRACT

A two-dimensional lattice or mesh scaffold for therapeutic cell implants is disclosed as well as methods for manufacture and use. The lattice is constructed of crisscrossing capillaries of hydrophobic parylene, such as parylene AF4, that may be coated with a hydrophilic polymer, such as parylene C, for cell adhesion. At each intersection of the crisscross, the intersecting capillaries are internally connected so as to allow oxygen to flow freely within. The walls of the capillaries are thin enough to be permeable to oxygen, on the scale of a micron thick, so that oxygen can flow through the lattice and permeate through the capillary walls. For some implants, cells are sandwiched between two or more lattices, the cells being slightly held apart from aggregation with each other by the lattice holes. The implants may then be surgically implanted within a subject.

18 Claims, 8 Drawing Sheets

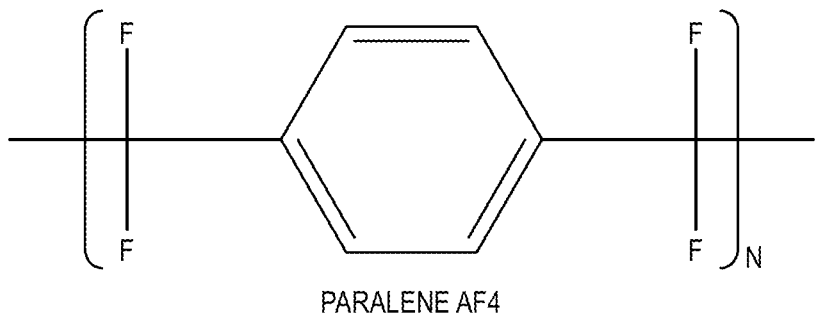

PARALENE AF4

1001
PROVIDE A PLURALITY OF TWO-DIMENSIONAL LATTICES, EACH LATTICE COMPRISING INTERCONNECTED CAPILLARIES OF HYDROPHOBIC PARYLENE, THE CAPILLARIES INTERSECTING TO FORM AN ARRAY OF LATTICE HOLES THEREBETWEEN, THE HYDROPHOBIC PARYLENE CAPILLARIES HAVING WALLS BETWEEN 0.1 $\mu M$ AND 10 $\mu M$ IN THICKNESS SO AS TO BE PERMEABLE TO DIATOMIC OXYGEN, THE LATTICE HOLES HAVING A CENTER-TO-CENTER SPACING BETWEEN 1 $\mu M$ AND 500 $\mu M$, THE TWO DIMENSIONAL LATTICES HAVING THERAPEUTIC CELLS SANDWICHED THEREBETWEEN TO FORM AN IMPLANT

1002
SURGICALLY PLACE THE IMPLANT INTO A SUBJECT

FIG. 10

MICROCAPILLARY MESH OXYGEN TRANSPORTER FOR CELL TRANSPLANTATIONS

CROSS-REFERENCES TO RELATED APPLICATIONS

This application claims the benefit of U.S. Provisional Application No. 63/283,639, filed Nov. 29, 2021, which is hereby incorporated by reference in its entirety for all purposes.

STATEMENT AS TO RIGHTS TO INVENTIONS MADE UNDER FEDERALLY SPONSORED RESEARCH AND DEVELOPMENT

This invention was made with government support under Grant No. DK129958 awarded by the National Institutes of Health. The government has certain rights in the invention.

BACKGROUND

1. Field of the Art

Embodiments of the present invention generally relate to a prosthetic scaffold for implanting into a body therapeutic cells, such as cells of the pancreas, the scaffolding comprising a porous, hollow cross section parylene lattice mesh for oxygen diffusion to the cells.

2. Description of the Related Art

Cell transplantation is a promising treatment to recover lost cellular functions. This concept is exemplified by pancreatic islet transplantation as a treatment for type 1 diabetes (T1D). Accounted for about 10% of all diabetes cases, T1D is an autoimmune disease in which insulin-producing islets/β-cells are selectively destroyed, leading to a severe insulin deficiency and subsequently a high blood sugar level. While daily exogenous insulin injection remains the gold standard of T1D treatment, complications like erratic glycemic control or hypoglycemic unawareness still present life-threatening side effects to these patients.

Instead of daily insulin injection, pancreatic islet transplantation into the liver using cadaveric-donor-derived islets is a radical, but promising, measure to free patients from the burdens of insulin injection.

Recently, there are significant developments in stem-cell-derived insulin-producing β-cells. For the transplantation of those cells, the subcutaneous (subQ) site has been largely studied and is now clinically-approved to monitor and mitigate the potential risk of neoplastic complications due to the pluripotent nature of the stem cells. Unlike the conventional site of the liver, subQ has the advantages of an easy explanation and minimally invasive surgical procedure.

Nevertheless, it is well known that hypoxic stress in the microenvironment will lead to a significant decrease in insulin secretion capability and even cell death. The major drawback of the subQ implantation is the lack of oxygen supply until graft revascularization is established.

Various approaches have been studied to provide extra oxygen supply, including oxygen inhalation, co-culture with oxygen-releasing biomaterials, and local concentrated oxygen administration. While some of the approaches are undergoing pre-clinical/clinical trials, patients under these scenarios still require regular intervention.

There is a need in the art for better devices and methods to reduce hypoxia in transplanted cells that is more convenient, and practical, for patients.

BRIEF SUMMARY

Generally, a mesh or two-dimensional lattice of interconnected hollow tubes with extremely thin, gas-permeable walls are used as a scaffold to support cells that are transplanted into a body. The tubes are made of a hydrophobic parylene, or at least have a hydrophobic interior, so that water does not condense on the inside. Thin walls of parylene AF4 on the order of a micron in thickness are permeable to gaseous oxygen. The lumens of the hollow tubes are interconnected so that oxygen (or other gases) readily move from a perimeter of the lattice to the internal region, thereby distributing oxygen there. The holes in the lattice have a center-to-center spacing that is on the order of 1 to 500 microns (μm), which is on the scale of biological therapeutic cells of particular utility.

Two lattices can sandwich cells in between to gently contain the cells. The bumps formed by the lattice holes help space apart the cells so that they are less prone to natural aggregation, ideally keeping the cells in a monolayer. More lattices can sandwich further layers of cells.

Manufacturing lattices can be accomplished by chemical vapor deposition (CVD) of hydrophobic parylene to a prescribed thickness over a sacrificial screen of metal. An optional coating of hydrophilic parylene can be deposited to the outside. When the metal is dissolved, the lattice remains with interconnected hollow tubes.

Some embodiments of the invention are related to a scaffold apparatus for therapeutic cell implants. The apparatus includes a two-dimensional lattice of interconnected capillaries of hydrophobic parylene, the capillaries intersecting to form an array of lattice holes therebetween, the hydrophobic parylene capillaries having walls between 0.1 μm and 10 μm in thickness so as to be permeable to diatomic oxygen, the lattice holes having a center-to-center spacing between 1 μm and 500 μm.

The hydrophobic parylene can be parylene AF4. There can be a coating of parylene C over an outside of the hydrophobic parylene capillaries, wherein the parylene C coating has a thickness between 0.1 μm and 1.0 μm.

There can be therapeutic cells on the lattice. The cells can be pancreatic islet β cells configured to secrete insulin. A biocompatible hydrogel can surround a layer of the cells on the lattice. The lattice holes can be smaller than the cells, and the center-to-center spacing can be larger than the cells. For example, the center-to-center spacing can be between 40 μm to 1000 μm, thereby equivalent in size to human pancreatic islet cells.

The lattice holes can all be a same shape as each other on the lattice. The lattice holes can have a circular, triangular, square, pentagonal, hexagonal, or octagonal shape. The capillaries can have a constant cross section, and the shape of the lattice holes can tessellate. The lattice holes can have a right triangular, rectangular, trapezoidal, or other non-regular polygon shape.

The lattice holes can have multiple different shapes and be combined into larger units or tiles on the lattice.

A cross section of the capillaries can be circular, oval, square, rectangular, trapezoidal, pentagonal, hexagonal, heptagonal, or octagonal.

There can be a sealant around a perimeter of the lattice configured to seal ends of the capillaries. There can be pillars within the capillaries configured to prevent collapse of the capillaries.

Some embodiments are related to a cell therapy implant apparatus that includes a plurality of two-dimensional lattices, each lattice comprising interconnected capillaries of hydrophobic parylene, the capillaries intersecting to form an array of lattice holes therebetween, the hydrophobic parylene capillaries having walls between 0.1 µm and 10 µm in thickness so as to be permeable to diatomic oxygen, the lattice holes having a center-to-center spacing between 1 µm and 500 µm, and therapeutic cells sandwiched between the two-dimensional lattices.

The hydrophobic parylene can be parylene AF4.

There can be a coating of parylene C over an outside of each of the hydrophobic parylene capillaries, wherein the parylene C coating has a thickness between 0.1 µm and 1.0 µm.

There can be N layers of the cells and N+1 lattices sandwiching the layers of cells. There can be one layer of the cells sandwiched between two of the lattices.

The cells can be pancreatic islet β cells configured to secrete insulin.

The lattice holes of at least two of the lattices can be aligned with one another. The lattice holes of each lattice can all be a same shape.

There can be a biocompatible hydrogel surrounding a layer of the cells between at least two of the plurality of two-dimensional lattices, or at least traces of hydrogel that have been washed away.

Some embodiments are related to a method of surgically implanting a cell therapy implant. The method can include providing a plurality of two-dimensional lattices, each lattice comprising interconnected capillaries of hydrophobic parylene, the capillaries intersecting to form an array of lattice holes therebetween, the hydrophobic parylene capillaries having walls between 0.1 µm and 10 µm in thickness so as to be permeable to diatomic oxygen, the lattice holes having a center-to-center spacing between 1 µm and 500 µm, the two dimensional lattices having therapeutic cells sandwiched therebetween to form an implant, and placing the implant into a subject.

The hydrophobic parylene can be parylene AF4.

An outside of the hydrophobic parylene capillaries can be coated with a parylene C coating having a thickness between 0.1 µm and 1.0 µm.

The cells can be pancreatic islet β cells.

The lattice holes of at least two of the lattices can be aligned with one another. The lattice holes of each lattice can all be a same shape.

A biocompatible hydrogel can surround a layer of the cells between at least two of the plurality of two-dimensional lattices.

The implant can be placed in a subcutaneous site in the subject or a liver in the subject.

Some embodiments are related to a method of manufacturing a scaffold apparatus for therapeutic cell implants. The method includes providing a sacrificial screen of metal, the screen having holes with a center-to-center spacing between 1 µm and 500 µm, depositing hydrophobic parylene on the screen to a thickness between 0.1 µm and 10 µm, dissolving the sacrificial screen of metal, thereby leaving a two-dimensional lattice of interconnected capillaries of hydrophobic parylene having walls between 0.1 µm and 10 µm in thickness so as to be permeable to diatomic oxygen, the capillaries intersecting to form an array of lattice holes therebetween, the lattice holes having a center-to-center spacing between 1 µm and 500 µm.

The hydrophobic parylene can be parylene AF4.

The method can include depositing a coating of parylene C over an outside of the hydrophobic parylene capillaries to a coating thickness between 0.1 µm and 1.0 µm.

The method can include distributing therapeutic cells onto the lattice and sandwiching the cells between the lattice and another of the two-dimensional lattice.

The method can include distributing additional therapeutic cells onto one of the lattices and sandwiching the additional cells with yet another of the two-dimensional lattice. The method can further include compressing the sandwiched cells between the lattices in order to squeeze the cells to align with the lattice holes and separate the cells from each other.

The lattice holes of at least two of the lattices can be aligned with one another. The lattice holes of each lattice can all be a same shape.

The cells can be held within a biocompatible hydrogel during manufacture. The method can include washing away the biocompatible hydrogel.

The method can include forming the sacrificial screen of metal by photolithography and electrochemically polishing the screen to round a cross section of the metal.

The method can include cutting the lattice and applying a sealant around a perimeter of the lattice in order to seal ends of the capillaries.

The depositing can be through chemical vapor deposition (CVD).

BRIEF DESCRIPTION OF THE DRAWINGS

FIG. 9 is a diagram representing a monomer of parylene AF4.

FIG. 10 is a flowchart illustrating a process in accordance with an embodiment.

DETAILED DESCRIPTION

Figure 1:
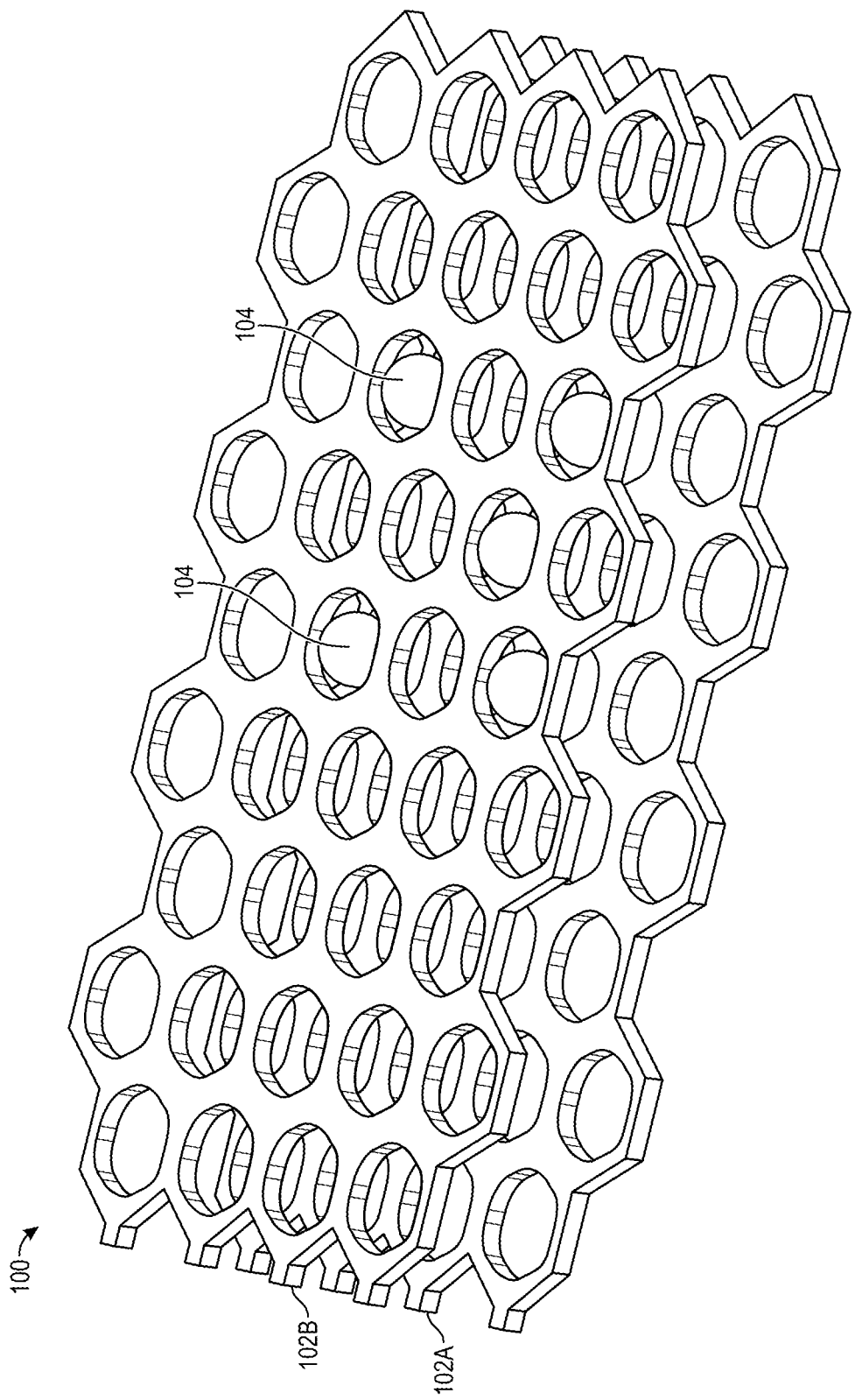
FIG. 1 is an isometric view of an implant device in accordance with an embodiment.

Cell transplantation is a way of treatment in which lost cellular functions can be recovered by transplanted cells. However, hypoxic conditions often happen on the transplanted site to hinder the survival of the cells. A flexible and thin polymeric microelectromechanical system (MEMS) oxygen-transporting hollow mesh structure can work as gas capillaries. These gas capillaries can effectively transport oxygen between microvessels and transplanted cells, maintaining adequate oxygen tension for cell survival and functionality.

Devices have demonstrated a 4-5 fold increase in cell viability compared to a control group without an oxygen-transporting mesh. Complications and interventions common with prior art methods for cell transplantation may be minimized and potentially eliminated.

Because of the high biocompatibility, maintenance-free properties, and scalability of embodiments, they have the potential as a clinical translational platform for not only pancreatic islet/β-cell transplantation to treat T1D but also any cell types at any transplantation sites for which efficacy is suffered from the hypoxic microenvironment.

A "hydrophilic" surface or untreated bulk material includes that having a static water contact angle that is less than or equal to 90°, or as otherwise known in the art.

A "hydrophobic" surface or untreated bulk material includes that having a static water contact angle that is greater than 90°, or as otherwise known in the art.

"Hydrophobic parylene" includes fluorinated parylene or surface-treated parylene such that its surface is hydrophobic, or as otherwise known in the art. Fluorinated parylene can include parylene AF4, also known by the trade name PARYLENE HT® polymer (trademarked by Specialty Coating Systems, Inc. of Indianapolis, Indiana, USA) in which the alpha hydrogen atom of the N dimer of parylene N is replaced with fluorine (see FIG. 9). Another parylene that is considered hydrophobic in bulk (without surface treatment) is parylene D.

In contrast, parylene N and parylene C are hydrophilic in bulk. Their surfaces can be treated to be hydrophobic and so may be considered hydrophobic only after such surface treatment.

"Crisscrossing" is multiple elongated elements intersecting each other to pass over or through multiple other elongated elements, or as otherwise known in the art. It can include intersecting at right angles (90°) or non-right angles.

A "diameter" of a hole includes a diameter of a circular hole, a distance across a non-circular closed-shape hole, or as otherwise known in the art. The distance across a non-circular hole can include the maximum or the minimum distance across the hole. For example in a square-shaped, unit sized hole, the minimum distance across is 1 unit, and the maximum distance, being the diagonal across the square, is the square root of 2 units. The simple average of the minimum and maximum distances is approximately 1.2 units.

A shape "tessellates" if multiple such shapes can be tiled or laid out in a lattice to fit together without gaps, or as otherwise known in the art.

FIG. 1 is an isometric view of an implant device in accordance with an embodiment. Implant device 100 includes two-dimensional lattice layers 102A and 102B. Each lattice layer is comprised of interconnected, hollow capillaries in a hexagonal mesh. The capillaries are formed from hydrophobic parylene.

Parylene is normally known as an impermeable material and, as such, is used for conformal coatings to weather seal electronics, medical devices, and other sensitive devices. However, when parylene is very thin, on the order of a micron, it is semipermeable. That is, it is permeable to some molecules but not others. Between about 0.1 µm and 10 µm in thickness, parylene AF4 is permeable to diatomic oxygen but impermeable to liquid water and large molecules. It is also permeable to water vapor; however, the hydrophobic internal surfaces of the capillaries prevent water vapor inside from condensing on the wall surfaces. Because liquid water cannot permeate the walls, and water vapor that can permeate the walls cannot condense on the walls, droplets of liquid water do not readily form within the capillaries. If they do form, the droplets remain relatively small. If a droplet does manage to grow large enough to block a capillary, there are numerous other paths within the capillaries for gases, such as oxygen, to flow. Thus, oxygen can flow easily through the internal lumens of the mesh's capillaries without being blocked by water. Importantly, it can flow from a perimeter of the mesh where there may be more oxygen to an internal region of the mesh where there is less. The oxygen in the internal region of the mesh can then permeate through the thin parylene walls to the outside, where cells are waiting.

In the figure, therapeutic cells 104 are held between the lattice layers 102a and 102B. The bumpy surfaces and voids of the lattice holes keep the cells from aggregating together, which is their natural inclination. The hollow lattices capillaries supply them with oxygen. The oxygen moves within the capillaries from the perimeter, which may be much farther away than shown in the figure, to the interior of the mesh and then permeates through the capillary walls to be consumed by the cells. Meanwhile, the cells take in nutrients and discharge waste products—as well as their therapeutic chemicals—to the liquid fluid surrounding them. The fluid readily flows to and from the cells between the lattice holes. Importantly, therapeutic chemicals, such as insulin, migrate to local body tissues that need them.

In effect, the hollow lattices reduce oxygen diffusion resistance. They act as low resistance oxygen-transporting shunts in contrast to tissue, which has higher-resistance to transporting oxygen. Air, which is in the hollow capillaries, has an oxygen permeability that is about four orders of magnitude higher than that of tissue.

Normally, silicone would be considered when needing an oxygen permeable material. However, silicone's high porosity also gives it a high water transmission rate. When the thickness of silicone is downsized to the micron regime, water will likely condense inside micro-channels. The oxygen transport will then be blocked.

On the other hand, PARYLENE-HT® (PA-HT; SCS Coatings, Indianapolis, Indiana, USA), generically known as parylene AF4, is a USP Class VI biocompatible polymer used in coatings for implantable medical devices. It has good oxygen permeability and less water permeability. PA-HT's thin, conformal, and pinhole-free properties are all ideal for forming walls for air-containing micro-channels.

Figure 2:
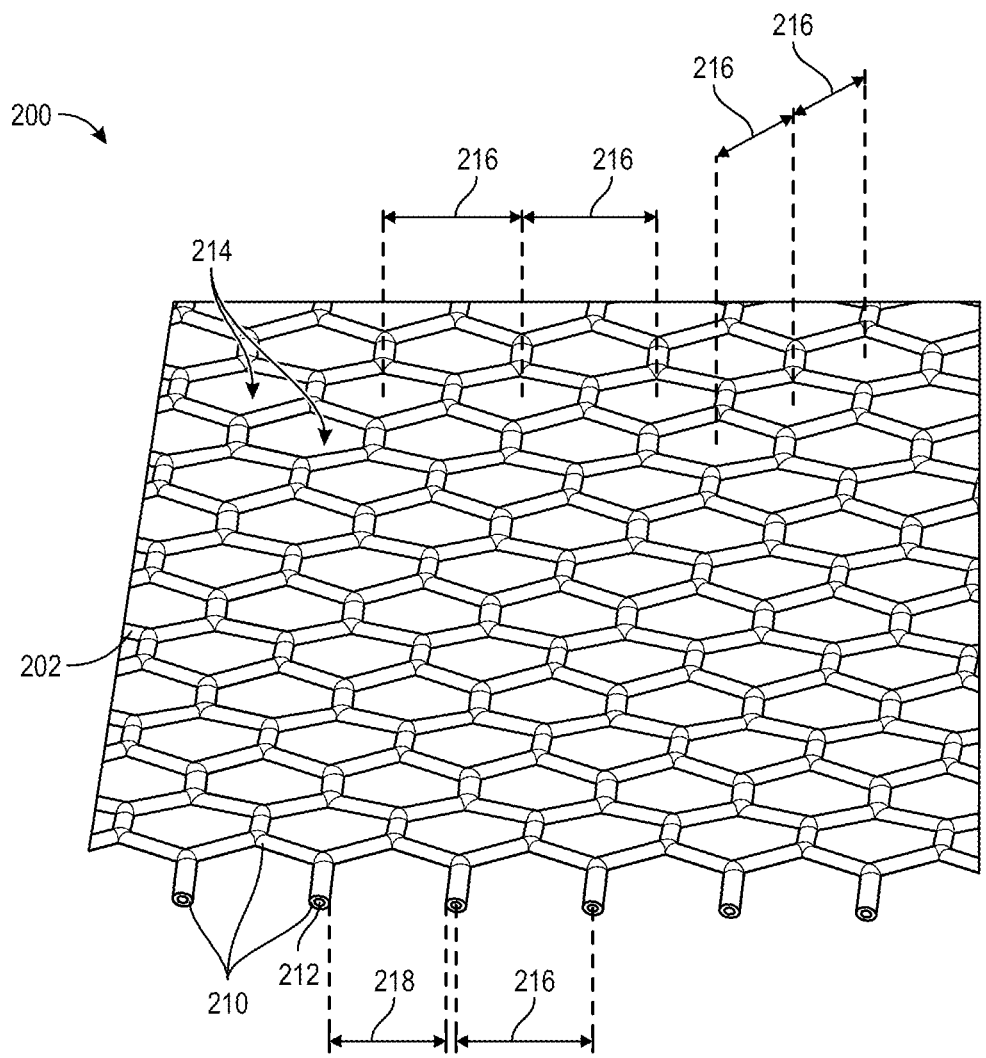
FIG. 2 is an isometric view of a hexagonal two-dimensional lattice in accordance with an embodiment.

FIG. 2 is an isometric view of a hexagonal two-dimensional lattice in accordance with an embodiment. In mesh system 200, lattice 202 employs skinnier capillaries than the lattices in FIG. 1, which, incidentally, better depict the capillary structure.

Lattice capillaries 210 connect with each other in a regular hexagonal pattern. Each capillary 210 has a hollow lumen 212. The walls of lumen 212 are hydrophobic.

The center-to-center distance between parallel lumens is distance 216 as measured as shown. This is the same length as the center-to-center distance between lattice holes 214. Center-to-center spacing of the lattice holes can be between 1 µm and 500 µm so as to hold cells. For example, a 40 to 1000 µm center-to-center spacing is about equivalent in size to human pancreatic islet β cells.

Given that the capillaries have a non-zero diameter, the gap or space between parallel capillaries is distance 218. If the lattice hole sizes 218 are smaller than the cells, and the center-to-center lattice spacing is larger than the cells, then the lattice holes can secure the cells so that they do not escape the lattice while keeping the cells separated from each other.

As an example, a hexagonal hollow mesh structure with an opening size of 200 µm can match the size of a cell or an islet. Each side of the hexagon can be composed of oxygen-transporting parylene AF4 channels with an inner hollow dimension of 25×25 µm². The thickness of the parylene is 1 µm to enable oxygen permeation and ensure proper mechanical strength at the same time.

The mesh holes of embodiments can be a circular, triangular, square, pentagonal, hexagonal, octagonal, or other regular or irregular polygonal shape. There may be multiple, different shapes within the same lattice, such as rectangles plus triangles, or they may be all the same shape as each other. The lattice elements or hole shapes can tessellate, such that they cover the plane without overlapping.

The lattice hole shapes can be irregular polygons, such as right triangles, rectangles, or trapezoids. There can be a mix of regular and irregular shapes. Regular polygons are shown in the figures, but irregular polygons are also envisioned.

Figure 3:
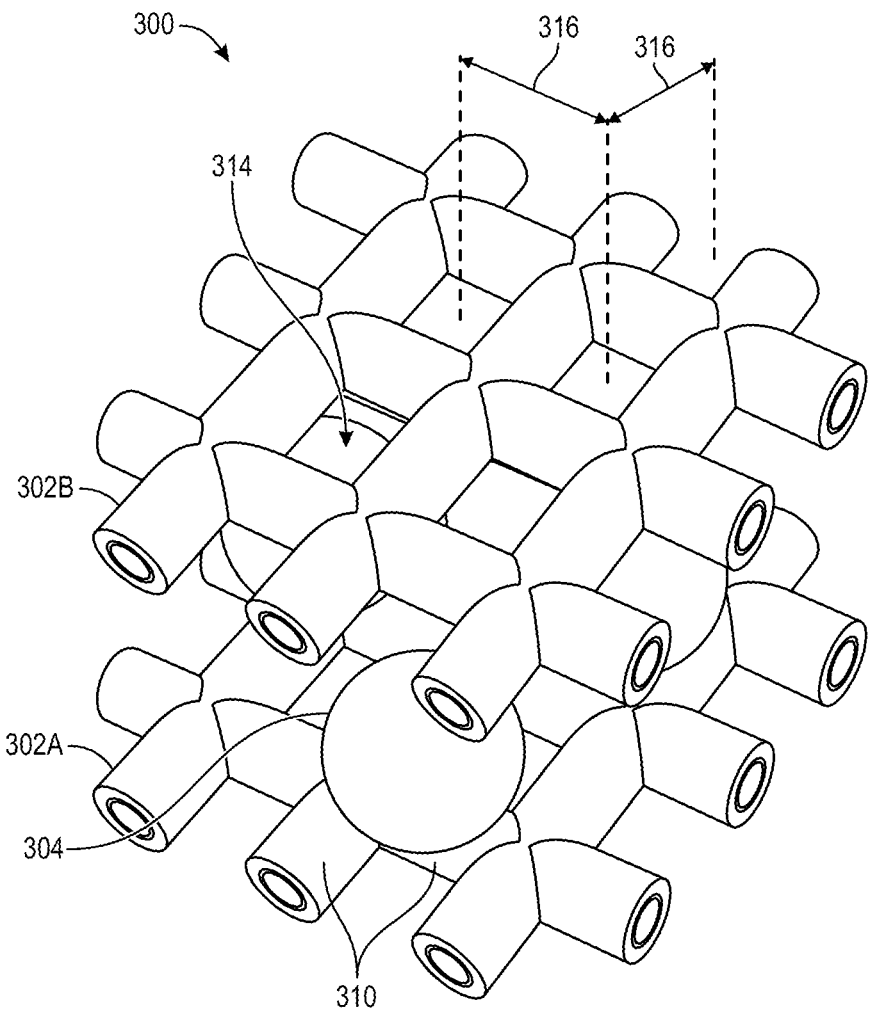
FIG. 3 is an isometric view of two layers of a square two-dimensional lattice with cells in accordance with an embodiment.

FIG. 3 is an isometric view of two layers of a square two-dimensional lattice with cells. In system 300, two lattice layers, 302A and 302B, are shown. Circular cross-section lattice capillaries 310 intersect at right angles to one another forming square lattice holes 314.

Because the lattice holes 314 are square, center-to-center spacing 316 is the same in two directions. Lattice holes 314 act as indentations to contain spherical cell 304.

Figure 4:
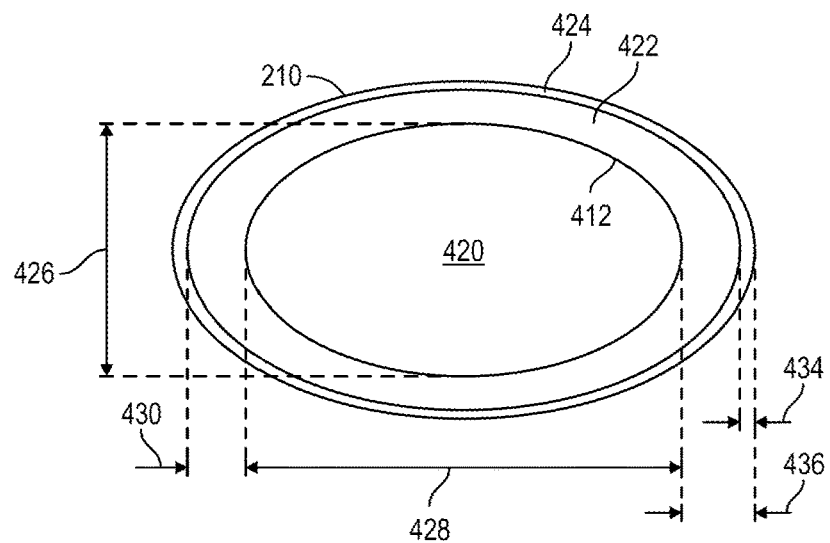
FIG. 4 is a cross-section of an oval capillary in accordance with an embodiment.

FIG. 4 is a cross-section of oval capillary 210, which was introduced in FIG. 2. Capillary 210 is comprised of hydrophobic parylene AF4 in inner wall portion 422 coated with a thin layer of parylene C coating 424. Interior 420 of capillary 210 is defined by surface 412 of inner wall portion 422. Because surface 412 is hydrophobic, it resists the formation of water droplets.

Inner wall portion 422 has thickness 430, while coating 424 has thickness 434. Coating thickness is between 0.1 µm and 1.0 µm, which helps cell adhesion. The total wall thickness 436 is the sum of inner wall thickness 430 and coating thickness 434. Total wall thickness 436 is 0.1 µm and 10 µm in thickness so as to be permeable to diatomic oxygen.

In addition to an oval external cross section, capillary 210 also has an oval internal cross section. Its internal cross section has major axis 428 and minor axis 426. Either the major axis or the minor axis can be selected to be in the same plane as the two-dimensional lattice. In some embodiments, the major (and minor) axes may be canted at an angle with respect to the plane of the two-dimensional lattice.

Figure 5:
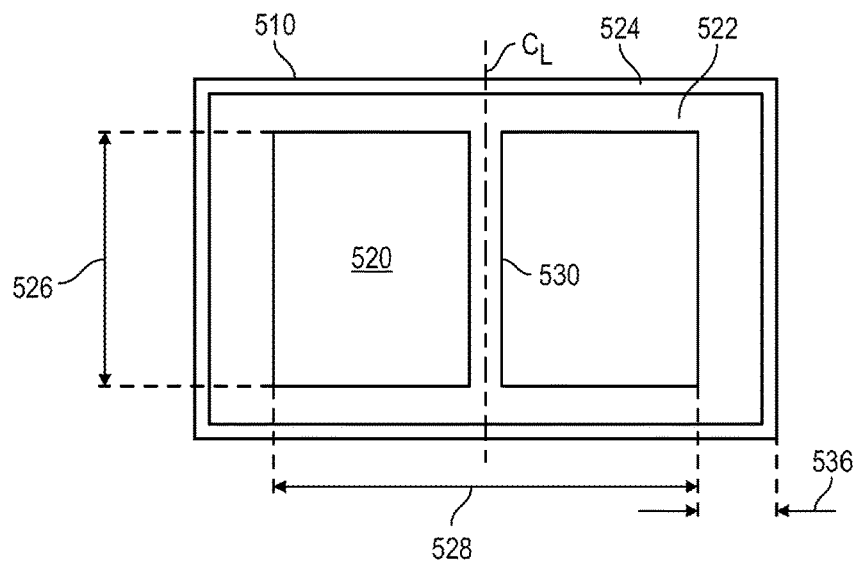
FIG. 5 is a cross-section of a rectangular capillary with pillars in accordance with an embodiment.

FIG. 5 is a cross-section of a rectangular capillary with pillars. Rectangular capillary 510 is formed from inner wall 522 with coating 524. The total wall thickness is the sum of the thicknesses of inner wall 522 and coating 524, which is wall thickness 536.

Capillary 510 is symmetric around a centerline through which multiple pillars 530 are set. The pictured cross section happens to be through one of the pillars. Otherwise, interior 520 of capillary 510 is free of obstructions, and air can flow from one side to the other. The pillars, set at predetermined or various distances along each capillary, can help prevent the collapse of the capillaries when pinched.

Rectangular capillary is longer in one direction than another and can be said to have internal dimensions of major axis 528 and minor axis 526.

Figure 6:
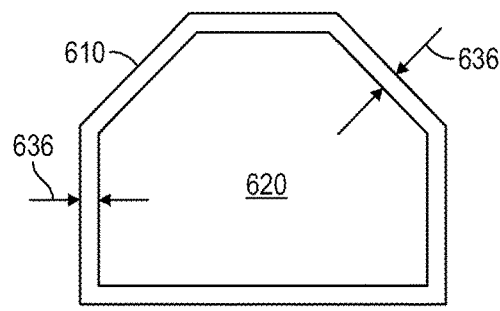
FIG. 6 is a cross-section of a six-sided polygon capillary in accordance with an embodiment.

FIG. 6 is a cross-section of a six-sided polygon capillary in accordance with an embodiment. Capillary 610 has six walls that each have thickness 636. The walls define interior 620. Although the cross section is not a regular polygon, it is symmetric around a vertical axis of the figure. Such a cross-section shape may help in lattice layers that are on the outside of a device in which there are more than two layers of lattices.

Figure 7:
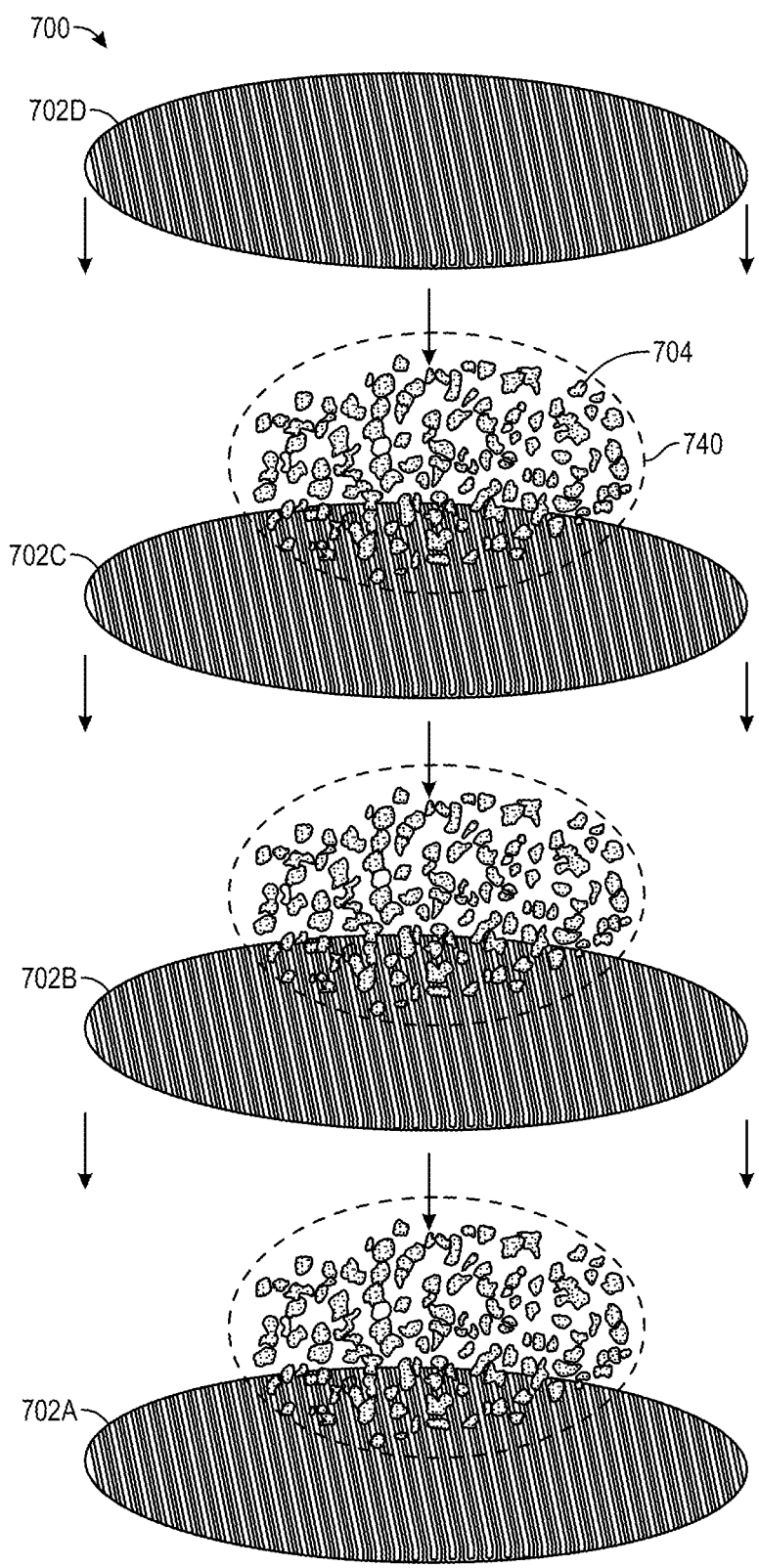
FIG. 7 is an exploded view of a three-cell-layer implant device in accordance with an embodiment.

FIG. 7 is an exploded view of a three-cell-layer implant device in accordance with an embodiment. In system 700, there are four layers of lattice 702A, 702B, 702C, and 702D encapsulating three layers of islet cells 704. The cells are surrounded by hydrogel 740 in order to corral them before dispersal within the mesh layers.

Two-dimensional lattices may be manufactured in large sheets and then cut to size for use. Or the lattices may be manufactured in small sections.

During assembly, the hydrogel layers of cells are set between the lattice layers. The assembly can then be lightly flattened in order to gently compress the sandwiched cells between the lattices. This squeezes the cells to align with the lattice holes and separate the cells from each other. This may work especially well if the lattice holes of are aligned with one another, or at least two of the lattice layers holes are aligned.

Two lattice layers and one cell layer may be assembled and compressed initially, and then additional therapeutic cells (optionally in hydrogel) can be distributed onto the top and then sandwiched with yet another of the two-dimensional lattice. After compression, other layers may be formed upon that. In this fashion, many-layered devices may be manufactured, such as those having 3, 4, 5, 6, 7, 8, 9, 10, 15, 20, or more layers of cells.

After the layers of lattices and cells are fully assembled and flattened, the hydrogel can be washed away. The hydrogel may also be left in place for implantation and may later dissolve and flush out within a subject.

Figure 8:
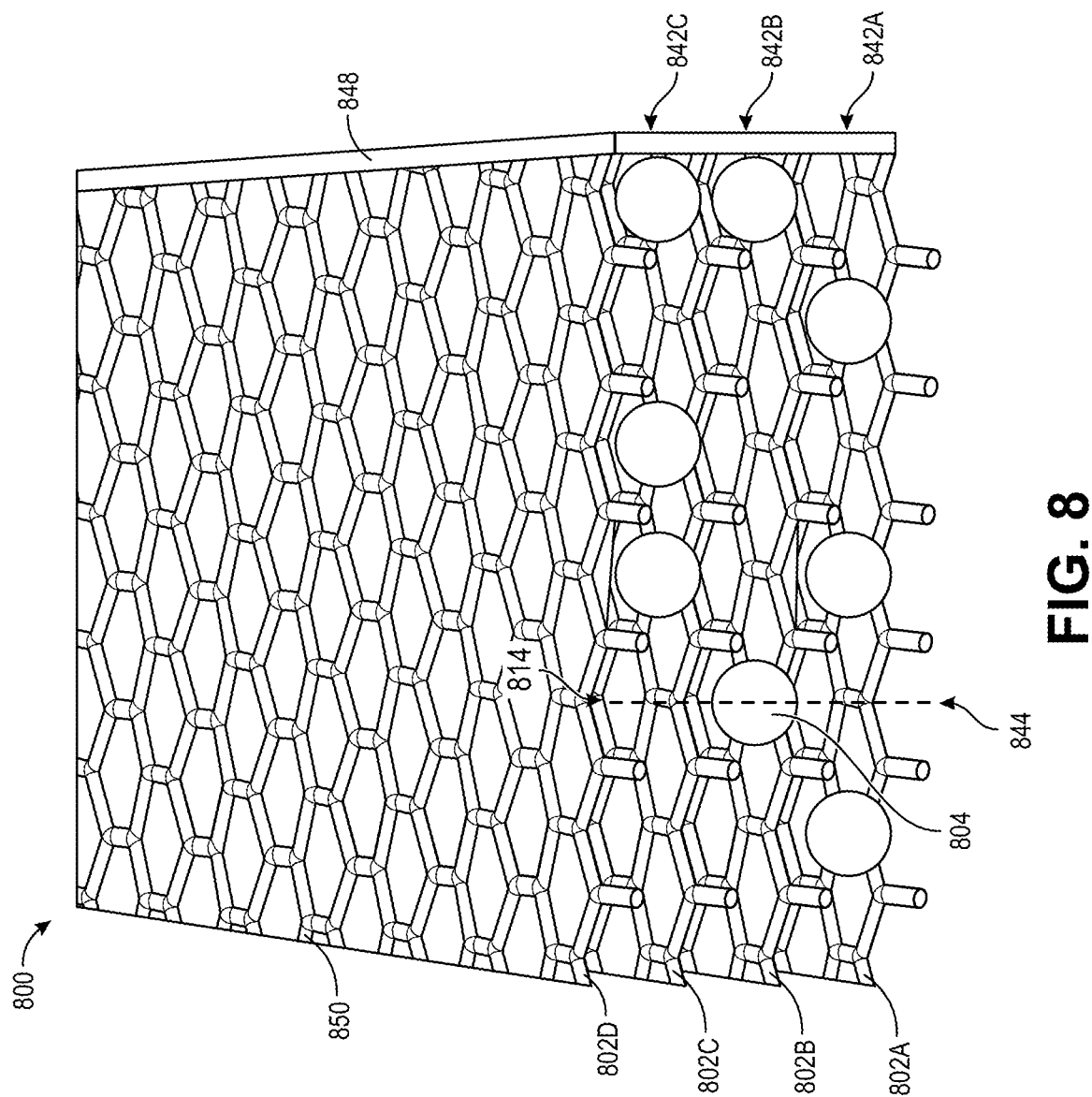
FIG. 8 is an isometric view of a three-cell layer implant device in accordance with an embodiment.

FIG. 8 is an isometric view of a three-cell layer implant device. In assembly 800 of this multi-layer device 850, lattice layers 802A, 802B, 802C, and 802D are mostly aligned with one another, as seen by line 844 running unimpeded through the holes 814 in the lattice layers. Between two of the layers, cell 804 is gently held in place between the holes.

Lattice layers 802A-D contain cell layers 842A, 842B, and 842C. That is, four lattice layers sandwich three cell layers. In any such system, N layers of the cells may be sandwiched by N+1 lattice layers.

Around a perimeter, for which one edge is shown in the figure, sealant 848 is applied so as to seal ends of the capillaries. Sealant may be unnecessary in some configurations because the hydrophobic nature of the inside of the capillaries prevents water and other liquids from ingressing very far into the capillaries, even with open, cut ends.

FIG. 9 is a diagram representing a monomer of parylene AF4, sometimes referred to as parylene AF-4 (with a dash) or PARYLENE HT® polymer. This parylene is one of several hydrophobic parylenes in bulk. Parylene AF4 may be deposited by chemical vapor deposition (CVD) in order to manufacture the lattices.

Figure 11:
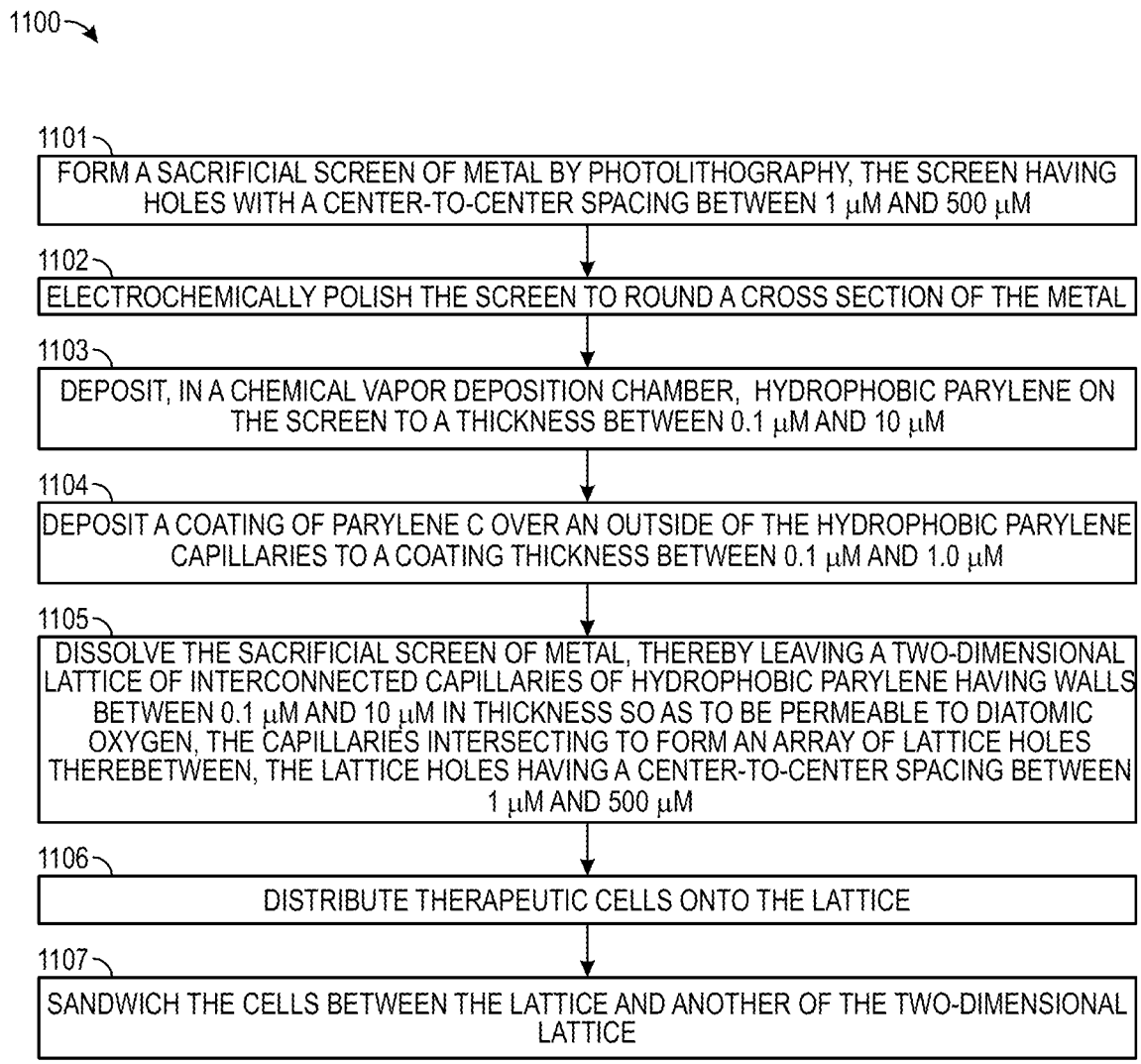
FIG. 11 is a flowchart illustrating a process in accordance with an embodiment.

FIG. 10 is a flowchart of process 1000 in accordance with an embodiment. In operation 1001, a plurality of two-dimensional lattices is provided, each lattice comprising interconnected capillaries of hydrophobic parylene, the capillaries intersecting to form an array of lattice holes therebetween, the hydrophobic parylene capillaries having walls between 0.1 µm and 10 µm in thickness so as to be permeable to diatomic oxygen, the lattice holes having a center-to-center spacing between 1 µm and 500 µm, the two-dimensional lattices having therapeutic cells sandwiched therebetween to form an implant. In operation 1002, the implant is surgically placed into a subject, for example in a subcutaneous site or a liver in the subject FIG. 11 is a flowchart of process 1100 in accordance with an embodiment. In operation 1101, a sacrificial screen of metal is formed by photolithography, the screen having holes with a center-to-center spacing between 1 μm and 500 μm. In operation 1102, the screen is electrochemically polished to round a cross section of the metal. In operation 1103, hydrophobic parylene is deposited, in a chemical vapor deposition chamber, on the screen to a thickness between 0.1 μm and 10 μm. In operation 1104, a coating of parylene C is deposited over an outside of the hydrophobic parylene capillaries to a coating thickness between 0.1 μm and 1.0 μm. In operation 1105, the sacrificial screen of metal is dissolved, such as by an etchant, thereby leaving a two-dimensional lattice of interconnected capillaries of hydrophobic parylene having walls between 0.1 μm and 10 μm in thickness so as to be permeable to diatomic oxygen, the capillaries intersecting to form an array of lattice holes therebetween, the lattice holes having a center-to-center spacing between 1 μm and 500 μm. In operation 1106, therapeutic cells are distributed onto the lattice. In operation 1107, the cells are sandwiched between the lattice and another of the two-dimensional lattice.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. "About" in reference to a temperature or other engineering units includes measurements or settings that are within ±1%, ±2%, ±5%, ±10%, or other tolerances of the specified engineering units as known in the art.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A scaffold apparatus for therapeutic cell implants, the apparatus comprising:
a two-dimensional lattice of interconnected capillaries of hydrophobic parylene, wherein the hydrophobic parylene is parylene AF4, the capillaries intersecting to form an array of lattice holes therebetween, the hydrophobic parylene capillaries having walls between 0.1 μm and 10 μm in thickness so as to be permeable to diatomic oxygen, the lattice holes having a center-to-center spacing between 1 μm and 500 μm.

2. The apparatus of claim 1 further comprising:
a coating of parylene C over an outside of the hydrophobic parylene capillaries, wherein the parylene C coating has a thickness between 0.1 μm and 1.0 μm.

3. The apparatus of claim 1 further comprising:
therapeutic cells on the lattice.

4. The apparatus of claim 3 wherein the cells are pancreatic islet β cells configured to secrete insulin.

5. The apparatus of claim 3 further comprising:
a biocompatible hydrogel surrounding a layer of the cells on the lattice.

6. The apparatus of claim 1 wherein the lattice holes are all a same shape.

7. The apparatus of claim 1 further comprising:
a sealant around a perimeter of the lattice configured to seal ends of the capillaries.

8. A cell therapy implant apparatus comprising:
a plurality of two-dimensional lattices, each lattice comprising interconnected capillaries of hydrophobic parylene, wherein the hydrophobic parylene is parylene AF4, the capillaries intersecting to form an array of lattice holes therebetween, the hydrophobic parylene capillaries having walls between 0.1 μm and 10 μm in thickness so as to be permeable to diatomic oxygen, the lattice holes having a center-to-center spacing between 1 μm and 500 μm; and
therapeutic cells sandwiched between the two-dimensional lattices.

9. The apparatus of claim 8 further comprising:
a coating of parylene C over an outside of each of the hydrophobic parylene capillaries, wherein the parylene C coating has a thickness between 0.1 μm and 1.0 μm.

10. The apparatus of claim 8 wherein there are N layers of the cells and N+1 lattices sandwiching the layers of cells.

11. The apparatus of claim 3 wherein the lattice holes are smaller than the cells and the center-to-center spacing is larger than the cells.

12. The apparatus of claim 1 wherein the center-to-center spacing is between 40 μm to 1000 μm, thereby equivalent in size to human pancreatic islet cells.

13. The apparatus of claim 6 wherein the lattice holes have a circular, triangular, square, pentagonal, hexagonal, or octagonal shape.

14. The apparatus of claim 6 wherein the capillaries have a constant cross section, and the shape of the lattice holes tessellate.

15. The apparatus of claim 6 wherein the lattice holes have a right triangular, rectangular, trapezoidal, or other non-regular polygon shape.

16. The apparatus of claim 1 wherein the lattice holes are multiple different shapes.

17. The apparatus of claim 1 wherein a cross section of the capillaries is circular, oval, square, rectangular, trapezoidal, pentagonal, hexagonal, heptagonal, or octagonal.

18. The apparatus of claim 1 further comprising:
    pillars within the capillaries configured to prevent collapse of the capillaries.

* * * * *